(12) United States Patent
Greer

(10) Patent No.: US 6,249,130 B1
(45) Date of Patent: Jun. 19, 2001

(54) SHIELDED FLAT-PLATE PROXIMITY/DIELECTRIC PROPERTIES SENSOR

(75) Inventor: Bryan D. Greer, Andover, MN (US)

(73) Assignee: AgriChem, Inc., Ham Lake, MN (US)

( * ) Notice: Subject to any disclaimer, the term of this patent is extended or adjusted under 35 U.S.C. 154(b) by 0 days.

(21) Appl. No.: 09/366,602

(22) Filed: Aug. 3, 1999

Related U.S. Application Data

(60) Provisional application No. 60/113,074, filed on Dec. 21, 1998.

(51) Int. Cl.[7] .................................................... G01R 27/26
(52) U.S. Cl. ............................................ 324/687; 324/664
(58) Field of Search .................................... 324/687, 664, 324/689, 658, 627

(56) References Cited

U.S. PATENT DOCUMENTS

| | | |
|---|---|---|
| 3,694,742 | 9/1972 | Bergmanis . |
| 4,099,118 * | 7/1978 | Franklin et al. ...................... 324/671 |
| 5,166,679 | 11/1992 | Vranish et al. . |
| 5,363,051 | 11/1994 | Jenstrom et al. . |
| 5,402,075 * | 3/1995 | Lu et al. ............................... 324/664 |
| 5,436,565 * | 7/1995 | Gammell ............................... 324/679 |
| 5,546,006 | 8/1996 | Louge . |
| 5,585,732 * | 12/1996 | Steele et al. ......................... 324/663 |
| 5,682,788 * | 11/1997 | Netzer ...................................... 73/73 |

OTHER PUBLICATIONS

J.R. Smith, Field Mice: Extracting hand geometry from electric field measurements, IBM Systems Journal, vol. 35, Nos. 3 & 4, 1996, pp 587–608, May 31, 1996.

* cited by examiner

*Primary Examiner*—Safet Metjahic
*Assistant Examiner*—Vincent Q. Nguyen
(74) *Attorney, Agent, or Firm*—Robert W. Gutenkauf

(57) ABSTRACT

A shielded flat-plate proximity/dielectric properties sensor includes a dielectric substrate leaving a planar configuration and a pair of spaced sensing electrodes mounted on one surface of the substrate. A pair of shield electrodes limit the electric field produced by the sensing electrodes. A first shield electrode on the back of the substrate intercepts field lines behind the sensor to prevent detection of objects from behind the sensor. A second shield electrode co-planar with and between the sensing electrodes intercepts field lines very close to the sensor to prevent the dense electric field near the sensor from dominating measurements of objects within the field.

4 Claims, 1 Drawing Sheet

SHIELDED FLAT-PLATE PROXIMITY/ DIELECTRIC PROPERTIES SENSOR

This application is based on provisional application Serial No. 60/113,074 filed Dec. 21, 1998.

BACKGROUND OF THE INVENTION

The present invention relates to a capacitive sensor for measuring material properties such as moisture or for detecting the presence or proximity of an object.

Most capacitive sensors for measuring material properties use a parallel plate or concentric cylinder design. The sensors work well in the laboratory or in a continuous stream of material, but certain applications require a less obtrusive sensor. Proximity sensors may be used to measure the dielectric properties of an object without entering or penetrating the object.

Proximity detectors typically measure capacitance between one conductor and ground and detect the presence of an object by noting the change in sensor capacitance when the object comes within the electric field generated between the sensor and a. reference potential. To measure in only one direction, such a sensor will typically be shielded on one side with a reference potential. This prevents observing objects on the shielded side but introduces a large measured capacitance which diminishes the sensitivity of the sensor.

BRIEF DESCRIPTION OF THE PRIOR ART

Attempts have been made to develop a capacitive sensor having a field which extends in one direction without diminishing sensitivity. The Vranish, et al., U.S. Pat. No. 5,166,679, for example, discloses a capacitive proximity sensing element which is backed by a reflector driver at the same voltage as the sensor. This results in an effective shield that does not increase the measured capacitance. However, complex circuitry is required to drive the shield.

The present invention was developed in order to overcome the drawbacks of the prior devices by providing a directional capacitive sensor with a high degree of sensitivity which does not require complicated circuitry to drive a shield.

SUMMARY OF THE INVENTION

Accordingly, it is a primary object of the invention to provide a capacitive sensor element including a dielectric substrate having a planar configuration, a pair of sensing electrodes arranged in spaced relation on one surface of the substrate, and shield electrodes arranged on the substrate. A first shield electrode is arranged on the opposite surface of the substrate from the sensing electrodes and parallel thereto. The first shield electrode interrupts and thus limits the measuring field defined by the electric field lines generated from one of the sensing electrodes when an electric current is supplied thereto. A second shield electrode is arranged on the same surface of the substrate as the sensing electrodes in co-planar relation. This shield electrode prevents the dense electric field very near the sensor element from severely dominating the capacitive measurement.

According to a more specific embodiment of the invention, the first and second shield electrodes are connected with a reference potential and the sensing electrodes are formed of a copper film.

According to a further object of the invention, the capacitive sensing element is incorporated into a shunt-mode capacitive sensing circuit including an operational amplifier. One of the sensing electrodes is connected with an input of the operational amplifier and a voltage source is connected with the other sensing electrode. A reference capacitor is connected across the operational amplifier between the one input and the output thereof.

BRIEF DESCRIPTION OF THE FIGURES

Other objects and advantages of the invention will become apparent from a study of the following specification, when viewed in the light of the accompanying drawing, in which.

DETAILED DESCRIPTION

Figure 2:
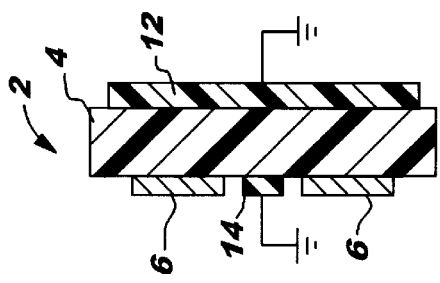
FIG. 2 is a sectional view of the sensor element taken along line 2—2 of FIG. 1.
Figure 1:
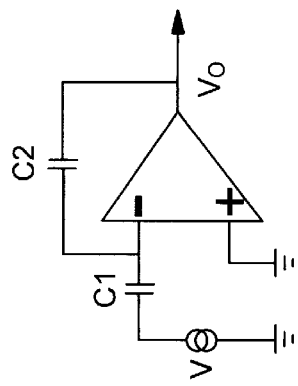
FIG. 1 is a front plan view of the capacitive sensor element according to the invention.
Figure 3:
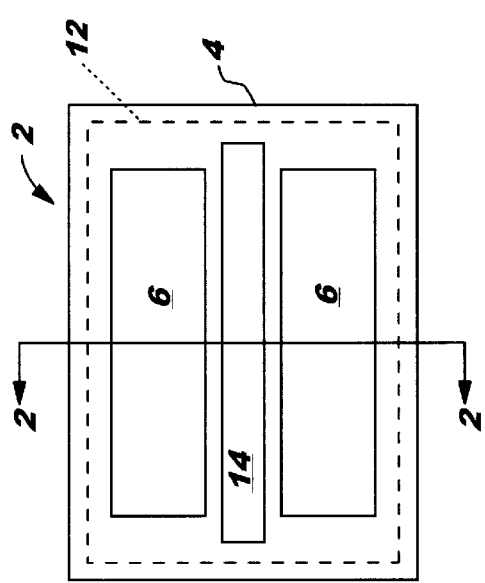
FIG. 3 is a side plan view of the sensor element of FIG. 1 showing the electric field lines generated by the sensing electrodes.

The capacitive sensor element according to the invention will be described with reference to FIGS. 1–3. The element 2 includes a substrate 4 formed of printed circuit board material and having a planar configuration. On one surface of the substrate is provided a spaced pair of sensing electrodes 6. The electrodes are coplanar as shown in FIGS. 2 and 3 and preferably have a rectangular configuration. However, it will be appreciated by those of ordinary skill in the art that other configurations (i.e., concentric rings) may be used for the sensing electrodes so long as they are spaced from one another. The sensing electrodes are formed of a conductive material. In a preferred embodiment, the electrodes are formed of a copper film.

When current is applied to one of the sensing electrodes 6a from a current supply 8, electric field lines 10 are generated from that electrode to the other electrode 6b as shown in FIG. 3. Collectively, the lines define the electric field for the sensing element as will be developed in greater detail below.

Two shield electrodes are also mounted on the substrate, both shield electrodes being connected with a reference potential. The first shield electrode 12 is arranged on the surface of the substrate opposite the surface on which the sensing electrodes are arranged as shown in FIGS. 2 and 3. The first shield electrode has a configuration similar to but less than that of the substrate and is arranged parallel to the sensing electrodes. Referring to FIG. 3, the first shield electrode 12 intercepts or blocks electric field lines 10 from extending to the rear or opposite surface of the sensing element. Thus, the sensor only measures or detects objects within the 180° field on the sensing electrode side of the element. Interference from behind the element, i.e., that side on which the first shield element is arranged, is prevented.

A second shield electrode 14 is arranged on the front surface of the dielectric substrate between and co-planar with the sensing electrodes 6 in spaced parallel relation. The second shield electrode intercepts or blocks the field lines 10 closest to the sensing element as shown in FIG. 3. This prevents the densest portion of the electric field very near the element from severely dominating capacitive measurements.

If desired, a protective dielectric layer can be provided over the sensing electrodes 6, second shield electrode 14 and the remainder of the one surface of the dielectric substrate 4.

According to the invention, the useful field lines are those which originate in the sensing electrode 6a and terminate in the sensing electrode 6b: These field lines are forced outwardly into the object or material being sensed. As an object enters the useful field lines, the change in capacitance between the sensing electrodes is detected (for proximity detectors) or measured (for content measuring devices). More particularly, the dielectric properties of a material or object are detected and measured. This is particularly useful for measuring properties such as moisture content of a particulate solid.

The shape and size of the sensing and shield electrodes will determine the sensing range of the capacitive sensing element according to the invention. Larger sensing electrodes spaced farther apart and wide coplanar shield electrodes will provide more distant sensing, while smaller and more closely spaced electrodes will provide measurements closer to the element.

Figure 4:
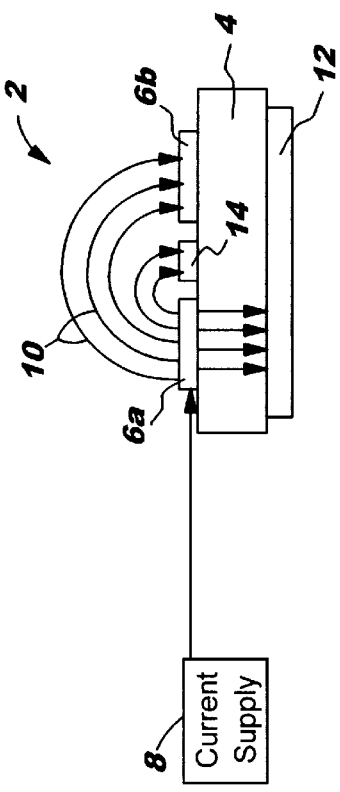
FIG. 4 is a diagram of the shunt-mode capacitive sensing circuit according to the invention.

Referring now to FIG. 4, there is shown a shunt mode capacitive circuit including a voltage source V, a pair of capacitors C1, C2, and an operational amplifier 16. Preferably, the capacitor C1 is a capacitive sensor element as described in FIGS. 1–3. One sensing electrode of the element C1 is connected with the voltage source, and the other sensing electrode of the element C1 is connected with an input of the operational amplifier. The capacitor C2 is a reference capacitor connected between the first input to the operational amplifier and the output of the operational amplifier. The other input to the operational amplifier is connected to ground. The output amplitude $V_0$ of the amplifier circuit is proportional to both the input voltage V and the capacitance C1 and inversely proportional to the capacitance C2 at whatever frequency is chosen for the sinusoidal input voltage V. The shield electrodes of the capacitive sensor element C1 are connected to ground. The output $V_0$ of the amplifier is processed by additional circuitry (not shown) depending on whether moisture content or proximity is being measured or detected, respectively. It will be appreciated that in an alternative configuration, the capacitor C2 may comprise a capacitive sensor element and the capacitor C1 is a reference capacitor.

While in accordance with the provisions of the patent statute the preferred forms and embodiments of the invention have been illustrated and described, it will be apparent to those of ordinary skill in the art that various changes and modifications may be made without deviating from the inventive concepts set forth above.

What is claimed is:

1. A capacitive sensor element, comprising:
   (a) a dielectric substrate having a planar configuration;
   (b) a pair of sensing electrodes arranged on one surface of said substrate in spaced relation; and
   (c) shielding electrode means being grounded and arranged between and parallel to said pair of sensing electrodes for interrupting at least a portion of the electric field lines generated from one of said sensing electrodes when an electric current is supplied thereto, thereby to direct the electric field lines in a given direction while preventing interference from the dielectric substrate, said shielding electrode means comprising
      (1) a first shield electrode arranged on a surface of said substrate opposite said one surface, said first shield electrode being parallel to said sensing electrodes and limiting a measuring field defined by said electric field lines to 180° on said one surface of said dielectric substrate; and
      (2) a second shield electrode arranged on said one surface of said substrate between and co-planar with said sensing electrodes in spaced parallel relation to prevent the dense electric field very near the sensor element from severely dominating a measurement, whereby when a substance being measured is proximate the sensor element, changes in the electric field lines are detected as a function of the characteristics of the substance.

2. A capacitive sensor element as defined in claim 1, wherein said first and second shield electrodes are connected with a reference potential.

3. A capacitive sensor element as defined in claim 2, wherein said sensing electrodes are formed of a copper film.

4. A shunt-mode capacitive sensing circuit, comprising:
   (a) an operational amplifier having a pair of inputs;
   (b) a reference capacitor connected with one of said inputs of said operational amplifier; and
   (c) a capacitive sensing element connected with said one input of said operational amplifier, said capacitive sensing element comprising:
      (1) a dielectric substrate having a planar configuration;
      (2) a pair of sensing electrodes arranged on one surface of said substrate in spaced relation; and
      (3) shielding electrode means being grounded and arranged between and parallel to said pair of sensing electrodes for interrupting at least a portion of the electric field lines generated from one of said sensing electrodes when an electric current is supplied thereto, thereby to direct the electric field lines in a given direction while preventing interference from the dielectric substrate, whereby when a substance being measured is proximate the sensor element, changes in the electric field lines can be detected as a function of the characteristics of the substance.

* * * * *